United States Patent
Bangert et al.

(10) Patent No.: US 9,958,435 B2
(45) Date of Patent: May 1, 2018

(54) ARRANGEMENT AND PROCESS FOR OPTICAL ANALYSIS AND SPECIFIC ISOLATION OF BIOLOGICAL SAMPLES

(75) Inventors: Joachim Bangert, Erlangen (DE); Katja Friedrich, Erlenbach a. Main (DE); Walter Gumbrecht, Herzogenaurach (DE); Karsten Hiltawsky, Schwerte (DE); Peter Paulicka, Röettenbach (DE); Manfred Stanzel, Berching (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 181 days.

(21) Appl. No.: 14/118,723

(22) PCT Filed: Apr. 16, 2012

(86) PCT No.: PCT/EP2012/056872
§ 371 (c)(1),
(2), (4) Date: Dec. 2, 2013

(87) PCT Pub. No.: WO2012/159822
PCT Pub. Date: Nov. 29, 2012

(65) Prior Publication Data
US 2014/0106355 A1    Apr. 17, 2014

(30) Foreign Application Priority Data
May 20, 2011 (DE) ........................ 10 2011 076 238

(51) Int. Cl.
| | | |
|---|---|---|
| *G01N 33/50* | (2006.01) | |
| *G01N 1/28* | (2006.01) | |
| *B01D 63/08* | (2006.01) | |
| *B01L 3/00* | (2006.01) | |
| *G01N 15/10* | (2006.01) | |
| *G01N 1/04* | (2006.01) | |
| *G01N 1/40* | (2006.01) | |

(52) U.S. Cl.
CPC ......... *G01N 33/5091* (2013.01); *B01D 63/08* (2013.01); *B01L 3/508* (2013.01); *G01N 1/2813* (2013.01); *B01L 2300/0681* (2013.01); *B01L 2300/0822* (2013.01); *G01N 2001/045* (2013.01); *G01N 2001/4088* (2013.01); *G01N 2015/1006* (2013.01)

(58) Field of Classification Search
CPC ............. G01N 33/5091; G01N 1/2813; G01N 2001/045; G01N 2001/4088; G01N 2015/1006; B01D 63/08; B01L 3/508; B01L 2300/0681; B01L 2300/0822
USPC .......................................................... 435/39
See application file for complete search history.

(56) References Cited

U.S. PATENT DOCUMENTS

| | | | |
|---|---|---|---|
| 3,731,806 A | | 5/1973 | McCormick |
| 4,124,449 A | | 11/1978 | Barta et al. |
| 5,022,411 A | * | 6/1991 | Guirguis ............ A61B 10/0045 600/584 |
| 5,321,545 A | * | 6/1994 | Bisconte ....................... 359/391 |
| 5,411,893 A | * | 5/1995 | Eden ........................ C12Q 1/04 356/244 |
| 5,663,057 A | | 9/1997 | Drocourt et al. |
| 5,891,394 A | | 4/1999 | Drocourt et al. |
| 5,905,038 A | | 5/1999 | Parton |
| 7,776,273 B2 | * | 8/2010 | Baer ..................... G01N 1/2813 422/527 |
| 2001/0014472 A1 | | 8/2001 | Tominaga et al. |
| 2003/0082516 A1 | | 5/2003 | Straus |
| 2003/0143580 A1 | | 7/2003 | Straus |
| 2003/0170613 A1 | | 9/2003 | Straus |
| 2004/0063169 A1 | | 4/2004 | Kane |
| 2009/0315987 A1 | | 12/2009 | Straus |
| 2010/0086959 A1 | | 4/2010 | Pflanz |
| 2010/0129912 A1 | | 5/2010 | Su et al. |
| 2010/0184629 A1 | * | 7/2010 | Giffin ....................... B01L 9/52 506/33 |
| 2010/0216183 A1 | | 8/2010 | Okanojo et al. |
| 2010/0248281 A1 | | 9/2010 | Straus |
| 2011/0076684 A1 | | 3/2011 | Frey et al. |

(Continued)

FOREIGN PATENT DOCUMENTS

| | | |
|---|---|---|
| CN | 101236195 A | 8/2008 |
| DE | 69603482 T2 | 11/1999 |

(Continued)

OTHER PUBLICATIONS

Abramowitz and Davidson (2003, Internet Archive capture). "Immersion Media", 7 pages.*
Kapuscinski (1995). DAPI: a DNA-Specific Fluorescent Probe. Biotech Histochem, v70(5), p. 220-233.*
"History of the Gram Stain and How it Works". Internet Article (2002), 1 page.*
International Search Report PCT/ISA/210 for PCT/EP2012/056872 dated Jul. 19, 2012.

(Continued)

*Primary Examiner* — Sean C. Barron
(74) *Attorney, Agent, or Firm* — Kevin Stein

(57) ABSTRACT

A process is disclosed for detecting cells in a liquid sample, which includes: i) filtration of the liquid sample through a porous membrane which is suitable for retaining detectable cells, where at least one subregion of a support is configured as transparent supporting body and the membrane is arranged over its area on the transparent supporting body in such a way that detectable cells are retained on at least part of the surface of the membrane and that at least part of the sample liquid passes through the membrane, ii) application of a liquid optical medium which has essentially the same refractive index as the supporting body, and iii) optical measurement of at least a subarea of the membrane in order to detect detectable cells.

20 Claims, 1 Drawing Sheet

(56) References Cited

U.S. PATENT DOCUMENTS

| | | | |
|---|---|---|---|
| 2012/0021435 A1 | 1/2012 | Hiltawsky et al. | |
| 2012/0315664 A1 | 12/2012 | Friedrich et al. | |
| 2014/0106388 A1 | 4/2014 | Bangert et al. | |

FOREIGN PATENT DOCUMENTS

| | | |
|---|---|---|
| DE | 60211140 T2 | 2/2007 |
| DE | 102007014082 A1 | 9/2008 |
| DE | 102010001322 A1 | 8/2011 |
| DE | 102010032081 A1 | 1/2012 |
| EP | 0713087 A1 | 5/1996 |
| EP | 1260807 A1 | 11/2002 |
| EP | 2199798 A1 | 6/2010 |
| JP | H06226063 A | 8/1994 |
| WO | WO-2003/022999 A2 | 3/2003 |
| WO | WO-2011/092201 A1 | 8/2011 |

OTHER PUBLICATIONS

Written Opinion PCT/ISA/237 for PCT/EP2012/056872 dated Jul. 19, 2012.

Office Action dated Nov. 4, 2014 issued in Chinese Patent Application No. 201280035947.5—Chinese Only.

International Preliminary Report on Patentability and Written Opinion dated Nov. 20, 2013 issued in PCT Application No. PCT/EP2012/056872—Full English Translation Only.

Office Action dated Jul. 11, 2012 issued in German Application No. 102011076238.8—German Only.

Whatman—GE Healthcare (2009) "Nuclepore track-etched membranes", <www.whatman.com/products.aspx?PID=20> retrieved Jul. 5, 2012.

International Preliminary Report on Patentability dated Nov. 20, 2013 issued in PCT Patent Application No. PCT/EP2012/056802—With English Translation.

International Preliminary Report on Patentablility dated Nov. 20, 2013 issued in PCT Application No. PCT/EP2012/056872—with Full English Translation.

International Search Report and Written Opinion dated Jul. 19, 2012 issued in PCT Patent Application No. PCT/EP2012/056872.

International Search Report and Written Opinion dated Jul. 31, 2012 issued in PCT Patent Application No. PCT/EP2012/056802—with Full English Translations.

Lin, H.K., et al. "Portable filter-based microdevice for detection and characterization of circulating tumor cells", *Clin. Cancer Research*, (2010), 16(20):5011-5018.

Office Action dated Jul. 28, 2014 issued in Chinese Application No. 201280030928.3—English Translation Only.

Office Action dated Jul. 28, 2015 issued in U.S. Appl. No. 14/118,701.

Office Action dated Jan. 5, 2012 issued in German Application No. DE 2011P02778.

Zheng, S., et al. "3D microfilter device for ciable circulating tumor cells (CTC) enrichment from blood", *Biomed. Microdevices*, (2011), 13(1):203-213.

Ognjanovic et al. (2005). Pre-B-cell colony-enhancing factor is a secreted cytokine-like protein from the human amniotic epithelium. American Journal of Obstetrics and Gynecology, v193, p. 273-282.

Matsudaria (1987). Sequence from Picomole Quantities of Proteins Electroblotted onto Polyvinylidene Difluoride Membranes. JBC, v262, p. 10035-10038.

\* cited by examiner

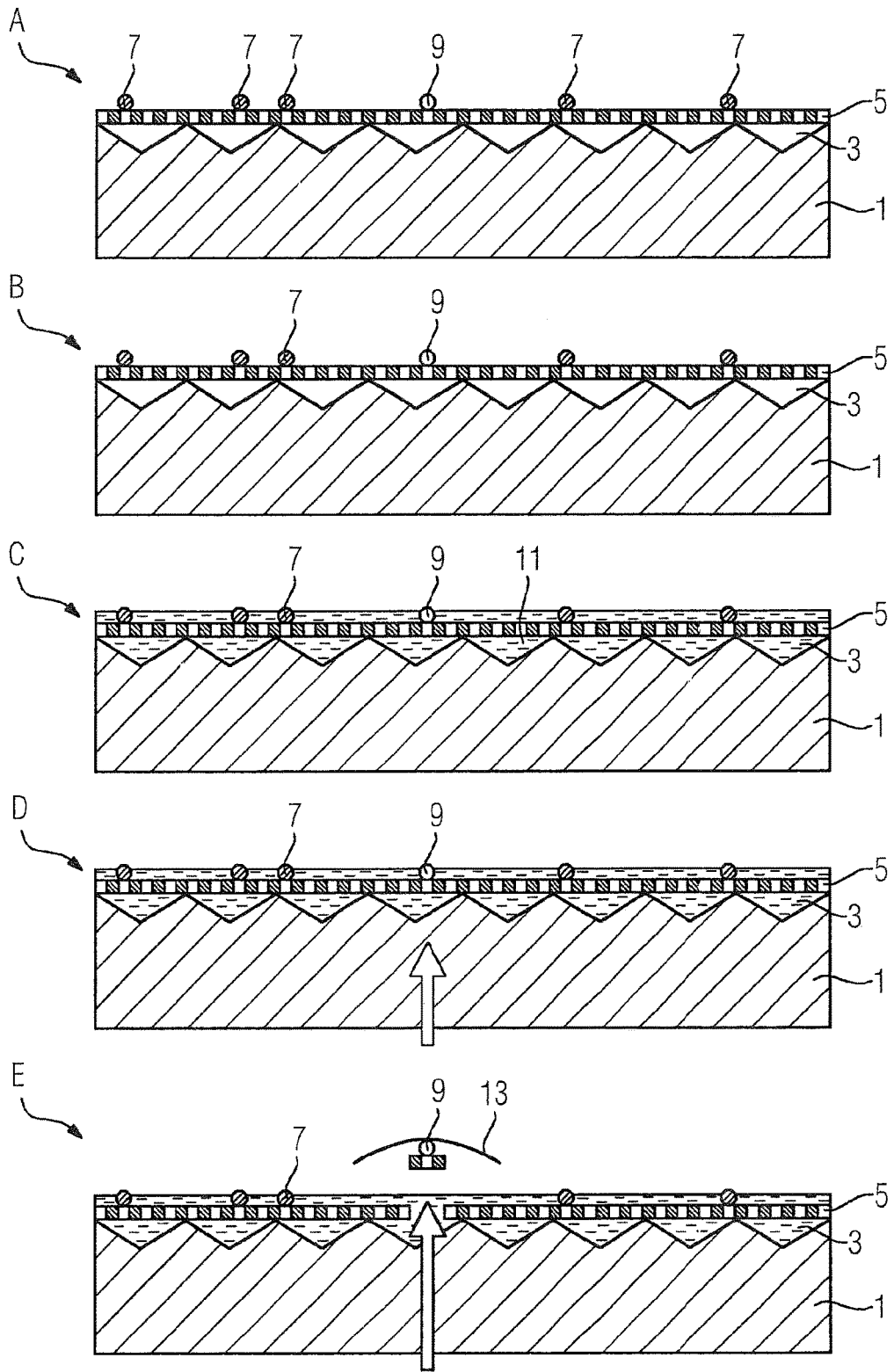

ARRANGEMENT AND PROCESS FOR OPTICAL ANALYSIS AND SPECIFIC ISOLATION OF BIOLOGICAL SAMPLES

PRIORITY STATEMENT

This application is the national phase under 35 U.S.C. § 371 of PCT International Application No. PCT/EP2012/056872 which has an International filing date of Apr. 16, 2012, which designated the United States of America and which claims priority to German patent application number DE 10 2011 076 238.8 filed May 20, 2011, the entire contents of each of which are hereby incorporated herein by reference.

FIELD

At least one embodiment of the invention generally relates to a process for detecting cells in a liquid sample and/or an arrangement that can be used to perform the process.

BACKGROUND

Microscopy is a widely used method of analysis. Especially in the "life sciences," it is an indispensable tool for, for example, characterizing tissues and cells. The slide has become established as the "interface" between the medium to be examined and the components of a microscope to be imaged. The slide is a glass plate with dimensions of 26×76 mm (ISO 8255-2) and a thickness of 1 to 1.5 mm. For example, the objects are applied to the slide in a thin layer (tissue section, liquid film) and usually covered with a cover glass (frequently 18 mm×18 mm; 0.16 mm thick). The filtration technique is likewise a widely used laboratory technique, especially for separating solids of various sizes or liquids.

In the combination of microscopy and filtration technique, the filter residue is examined microscopically following the filtration process. For this purpose the filter medium, e.g., the filtration membrane, must be removed from the filtration device and placed on the slide. This process requires high experimental deftness, especially in the case of thin membranes (e.g., 10 μm thick, 25 mm diameter) and is very time-consuming. In order for this process to be used routinely and cost-effectively, for example in medical diagnostics, e.g., in the examination of tumor cells filtered from a blood sample, it would be necessary to develop a simple and cost-advantageous solution that can be performed even by untrained personnel. In particular, isolation of selected individual cells, such as circulating tumor cells (mCTCs), or cell clusters for subsequent molecular diagnostic examination will be of increasing significance in the future because of the scientific advances made in this area.

SUMMARY

At least one embodiment of the present invention is directed to an arrangement and/or a process for optical analysis and specific isolation of biological samples which can be used in standard processes with high quality and are simple in design and easy to use as well as cost-effective. In particular, an embodiment of the present invention is directed to an arrangement and a process for optical analysis and specific isolation of biological samples which are very suitable for subsequent microscopic examination. The arrangement should be usable in standard equipment with standard holders in order to permit, for example, serial optical microscopic or fluorescence microscopy examinations of the filtration residue to be performed simply and inexpensively. In particular, it is a goal to permit its use in the collection and examination of (circulating) tumor cells (CTC).

In a filtration process in the sense of at least one embodiment of the invention, a suspension is filtered through a filter, e.g., a filter membrane. In this process, permeate is forced through the filter and retentate is retained on the filter surface (or in the pores and cavities of the filter). Therefore, during the filtration process there is a predominant flow direction of the permeate through the filter, so that it is possible to speak of an area upstream from the filter, in which the retentate (which contains the cells as its essential component) is retained, and an area downstream, in which the permeate is forced through and can, for example, be collected there. Independent of this predominant flow direction, in exceptional instances the flow direction can also be reversed, for example during back-washing of the filter.

At least one embodiment of the invention relates to a process for detection of cells in a liquid sample, comprising:
i) filtration of the liquid sample through a porous membrane that is suitable for retaining cells to be detected, wherein at least one subregion of a support is configured as a transparent supporting body and wherein the membrane is arranged in a flat configuration on the transparent supporting body in such a way that cells to be detected are retained on at least part of the surface of the membrane and that at least part of the sample liquid passes through the membrane,
ii) application of a liquid optical medium which has essentially the same refractive index as the supporting body, and
iii) optical measurement of at least a subarea of the membrane in order to detect cells to be detected.

At least one embodiment of the invention also relates to an arrangement for detection of cells in a liquid sample, comprising a support that is suitable for retaining cells to be detected, wherein the membrane is arranged in a flat configuration on a supporting body, wherein the supporting body is arranged and/or formed in a recess of a support and a liquid optical medium which has essentially the same refractive index as the supporting body, wherein at least the supporting body is transparent.

BRIEF DESCRIPTION OF THE DRAWINGS

In the following, the invention will be described by way of example based on the FIGURE.

The figure schematically illustrates an embodiment of the process according to the invention.

DETAILED DESCRIPTION OF THE EXAMPLE EMBODIMENTS

In a filtration process in the sense of at least one embodiment of the invention, a suspension is filtered through a filter, e.g., a filter membrane. In this process, permeate is forced through the filter and retentate is retained on the filter surface (or in the pores and cavities of the filter). Therefore, during the filtration process there is a predominant flow direction of the permeate through the filter, so that it is possible to speak of an area upstream from the filter, in which the retentate (which contains the cells as its essential component) is retained, and an area downstream, in which the permeate is forced through and can, for example, be collected there. Independent of this predominant flow direction, in exceptional instances the flow direction can also be reversed, for example during back-washing of the filter.

To force the permeate through the filter, a pressure difference can be created, wherein a higher pressure then prevails upstream from the filter than downstream. This can be achieved by applying a positive pressure upstream from the filter, applying a negative pressure downstream, or a combination of the two. To stop the flow of permeate through the filter (reduce it to zero), a zero pressure difference can be established. This is independent of the orientation of the filter in space. For the special case that the flow direction runs vertical to the filter or has a vertical component (thus in the direction of or opposite the direction of gravitational force), it should also be kept in mind that the hydrostatic head on the filter contributes to the pressure difference.

For some applications of the process according to at least one embodiment of the invention, it is preferred that the flow direction of the filtration on the filter essentially runs in the direction of gravitational force. In this way, retained retentate comes to lie on the surface of the filter, which for example permits simple further processing of the retentate (of the cells).

For certain applications it may be preferable to perform filtration not in the direction of gravitational force, but in the opposite direction to gravitational force, e.g., if the retentate floats or in order to collect cells from the underside of the filter in a collecting flask after filtration.

At least one embodiment of the invention relates to a process for detection of cells in a liquid sample, comprising:
iv) filtration of the liquid sample through a porous membrane that is suitable for retaining cells to be detected, wherein at least one subregion of a support is configured as a transparent supporting body and wherein the membrane is arranged in a flat configuration on the transparent supporting body in such a way that cells to be detected are retained on at least part of the surface of the membrane and that at least part of the sample liquid passes through the membrane,
v) application of a liquid optical medium which has essentially the same refractive index as the supporting body, and
vi) optical measurement of at least a subarea of the membrane in order to detect cells to be detected.

The membrane can be arranged on the supporting body. This serves to support the membrane and permit the filtrate to flow through. The membrane can lie against the supporting body. In addition, channels can be formed in the surface of the supporting body to guarantee the flow of filtrate.

According to an alternative embodiment, holes or pores may also be provided in the supporting body. The supporting body can be configured as a separate part in a recess of the support, but it may also be configured integrally with the support in one subregion of the support.

The refractive index n indicates the ratio of the speed of light in a vacuum c0 to the speed of propagation cM of light in medium M:

$$n=c0/cM.$$

The refractive index is a dimensionless number. An essentially identical refractive index means that the refractive index differs by no more than 0.1, preferably no more than 0.01, more preferably no more than 0.001.

The support preferably has essentially the dimensions of a microscopy slide.

For example, the membrane and the supporting body can have an essentially rectangular, round, or elliptical base area.

Through the use according to at least one embodiment of the invention of an optical medium that is matched with the material of the supporting body, the optical detection is substantially improved.

Preferably the membrane and the supporting body are selected such that they likewise have essentially the same refractive index.

According to one embodiment of the invention, the cells to be detected are labeled, before or after filtration, with a first element for labeling the cells to be detected which contains a first marker.

Suitable elements for labeling comprise markers that can stain cells specifically or nonspecifically. Nonspecific markers may be, for example, dyes that stain proteins, nucleic acids, or other cell constituents. Specific markers may be, for example, antibodies, oligonucleotide probes, peptides or other molecules that bind specifically to proteins, nucleic acid sequences or other cell-specific structures.

The marker can be directly labeled with a detectable label, e.g., chromogenic dyes, fluorescent dyes, isotope labeling or the like. Alternatively, the marker may also be detected using a secondary detection reagent (e.g., secondary antibody or enzyme-substrate system).

According to a preferred embodiment of the invention, in the process, after filtration the cells on the membrane are stained with a dye by incubating with an appropriate process liquid. For this purpose, dyes may be selected which stain cells or cell constituents and are known from cytology and histology. These may be vital or nonvital stains, stains that specifically stain cell nuclei or other organelles or that specifically stain certain cell components, e.g., nucleic acids or proteins. Known cell stains include for example Trypan Blue, DAPI and the like.

The cells to be detected can also be analyzed microscopically on the membrane, with or without staining.

The membrane lies in a flat configuration, preferably on the transparent supporting body (3) and covers it at least partially or also completely.

According to one embodiment of the invention, the support is a slide for microscopy which is made of glass or plastic, especially cyclic olefin copolymer (COC) or polycarbonate. A preferred COC is known under the trade name of TOPAS®.

According to one embodiment of the invention, the supporting body is textured and/or porous and made of plastic, cyclic olefin copolymer (COC) or polycarbonate, especially of the same material as the support.

According to one embodiment of the invention, the support and the supporting body are made integrally from a single body, and the membrane covers the recess in the support are complete and in particular is flat, especially is supported on the supporting body in plane-parallel fashion in the area of the recess.

According to one embodiment of the invention, the supporting body has channels formed on a side facing the filter membrane, the channels being configured in fluid contact with the filter membrane. The channels can be configured as openings in the supporting body and/or the support, as a result of which liquid can flow away from the membrane through the supporting body or support or can be suctioned away. The openings can be configured, for example, as perpendicular holes from top to bottom of the supporting body or support. The membrane and the supporting body, for example, can have an essentially rectangular, round or elliptical base area. The openings can be present at regular intervals at the edge of the base area.

This preferred arrangement allows uniform outflow of the filtrate. At the same time, the membrane essentially covers the supporting body, so that when the interstices between the membrane and the supporting body are filled with the optical medium, and also if the membrane pores become filled with the medium, an optical unit with a uniform refractive index forms, on which microscopy can be performed especially readily. Alternatively, the openings may also be distributed essentially uniformly over the base area of the supporting body.

According to one embodiment of the invention, the membrane and the supporting body form a mutual contact surface having a plurality of mutual contact points lying in a plane-parallel, flat plane of the contact surface, wherein especially the membrane has a maximum distance from the supporting body of less than 100 µm. The membrane preferably lies on the contact points.

According to one embodiment of the invention, the filter membrane (2) is a Track Etched filter membrane, that is composed of a polycarbonate film and has pores with a diameter of 2-100 µm, especially 5-20 µm, preferably 5-10 µm, more preferably about 8 µm.

According to one embodiment of the invention, one cell to be detected can be isolated. The isolated cell can then be characterized in further detail or subjected to further functional examinations.

According to one embodiment of the invention, the cell to be detected can be isolated by laser microdissection. Preferably, optical detection and subsequent laser microdissection can be performed in the same device in successive working steps.

Laser microdissection is a microscopic technique for laser-supported microdissection of tissues and cells. In this process, an individual cell or a desired region can be cut out of a tissue section with the aid of a laser (e.g., an infrared or ultraviolet laser). It is possible to "cut out" the cell together with the surface section of the membrane on which it is lying. The clean cell is then either isolated by dropping it into a reaction vessel under the influence of gravity, or it is catapulted into this against the force of gravity, or it is lifted off indirectly via the adhesive cover of the reaction vessel.

According to one embodiment of the invention, the cell to be detected is a tumor cell.

At least one embodiment of the invention also relates to an arrangement for detection of cells in a liquid sample, comprising a support that is suitable for retaining cells to be detected, wherein the membrane is arranged in a flat configuration on a supporting body, wherein the supporting body is arranged and/or formed in a recess of a support and a liquid optical medium which has essentially the same refractive index as the supporting body, wherein at least the supporting body is transparent.

An arrangement in the sense of an embodiment of the invention is considered to be an assembly ("kit of parts") consisting of a support, a membrane and the liquid optical medium. The membrane can be attached to the support and/or the supporting body, e.g., by bonding, welding, clamping or the like. According to a preferred embodiment, the membrane covers the supporting body and is connected to the support at its edge, e.g., by spot welding.

It is preferable for the support to be a microscopy slide made of glass or plastic, especially polycarbonate, and/or for the supporting body to be configured to be textured and/or porous, made of plastic, especially polycarbonate.

In FIG. 1 a sectional view of a flat supporting body 1 is shown, which for example consists of COC, especially for example of the COC with the trade name of TOPAS. Channels 3 are formed on the top of the supporting body 1, facing a membrane 5. These channels pass through the surface of the supporting body and can open into holes or openings (passing through the supporting body), through which liquids can be suctioned away from the surface of the supporting body.

Instead of providing channels, it is also possible to provide elevations on the surface of the supporting body, which for example are configured as truncated pyramids or cones, and the surfaces of which lie in a plane that defines a support surface or contact surface on which the membrane 5 is supported. According to a preferred embodiment, the surface of the supporting body is made up as a hexagonal packaging of 150 µm high truncated cones with a modular dimension of 300 µm. The interstices of the truncated cones form channels in which the liquid can run off and the truncated surfaces of the truncated coens define a support surface for the membrane.

A subregion of the support is configured as a supporting body. The support preferably has the dimensions of a slide such as is used in microscopy.

The pore size of the membrane is selected such that cells 9 to be detected cannot pass through the membrane.

The sample is now filtered in a first step A of FIG. 1, so that cells 9 to be detected now lie on the membrane.

The membrane has a pore size of 0.1 to 200 µm. As a result, cells can be retained, whereas cell fragments, platelets and smaller solid constituents of the sample pass through the filter (the membrane).

Preferably the membrane has a pore size of 2 to 50 µm, more preferably 5 to 20 µm, even more preferably 5 to 10 µm. Pore sizes in the size ranges of 2 to 50 µm, 5 to 20 µm or especially 5 to 10 µm offer the advantage that they retain the cells, but the cells partially stick within the pores and thus adhere particularly well to the membrane and are available for further analyses. A pore size of about 8 µm was found to be especially advantageous.

The cells to be separated from the sample liquid are separated in that they remain on the surface of a filter membrane that is impermeable for the solids to be separated (e.g., cells) but is permeable for the surrounding medium and also for the solids (e.g., cell fragments) contaminating the solids to be separated (cells).

In an optional step B of FIG. 1, cells 9 to be detected can be labeled so that they can be more readily distinguished from other cells 7. This can be done, for example, with an immunohistochemical stain of specific antigens. If tumor cells are to be detected, numerous known tumor antigens are available, which can be labeled with an appropriate antibody. In this way it is possible to detect specific tumor cells. Appropriate antibodies and staining protocols are known to the person skilled in the art.

The following list contains some preferred cell-specific antigens:

Alpha-1-fetoprotein (AFP) in the case of hepatocellular cancer and gonadal and extragonadal germ cell tumors Bence-Jones protein in the case of multiple myeloma Beta-HCG (beta subunit of human chorionic gonadotropin) in the case of germ cell tumors of the ovary and non-seminomatous tumors of the testicle CA 15-3 in the case of breast cancer or ovarian cancer CA 19-9 and CA 50 in the case of pancreatic cancer CA-125 in the case of ovarian cancer Calcitonin (human calcitonin, hCT) in the case of medullary thyroid cancer Carcinoembryonic antigen (CEA) in the case of intestinal cancer, pancreatic cancer and adenocarcinoma of the lung Cytokeratin-21 fragment (CYFRA 21-1) and serpin B4 (SCC) in the case of all variants of lung cancer (bronchial carcinoma)

HER-2/neu

HPV antibodies or HPV antigens

Homovanillic acid in the case of neuroblastoma 5-hydroxyindoleacetic acid in the case of carcinoid Catecholamines, vanillomandelic acid in the case of pheochromocytoma Lactate dehydrogenase (LDH) in the case of germ cell tumors Lactate dehydrogenase isoenzyme 1 (LDH-1) in the case of germ cell tumors; however, routine determination is not recommended in current guidelines MAGE antigens Metanephrine in the case of pheochromocytoma MUC1 in the case of non-small-cell lung cancer (NSCLC) or in the case of breast cancer NSE in the case of small-cell lung cancer (SCLC), neuroblastoma and seminomatous germ cell tumors Placental alkaline phosphatase (PLAP) in the case of seminomatous germ cell tumors PSA in the case of prostate cancer Thyroglobulin (Tg) at any concentration in the case of papillary or follicular thyroid cancer Thymidine kinase Cytokeratins, e.g., cytokeratin 8, 18, 19

Thus labeling makes it possible to recognize a specific cell type. Therefore it is possible, for example, to distinguish tumor cells to be detected from leukocytes in a blood sample. Alternatively or in addition, however, cells may also be labeled with a nonspecific stain (which does not distinguish between different cell types) for example a vital stain (e.g., Fluorescein) or a nonvital stain (e.g., Trypan Blue). In this way, for example, live or dead cells can be selected for further analysis.

In an additional step C of FIG. 1, a liquid optical medium 11 which has essentially the same refractive index as the supporting body is applied.

The liquid optical medium 11 is applied in such a manner that it fills the interstices between the membrane 5 and the supporting body 3, which are defined, for example, by the channel structure in the supporting body 3.

In addition, the liquid optical medium 11 also fills the pores of the membrane 5 and preferably also covers the surface of the membrane 5 and the cells lying on it in a thin layer.

Thus the optical imaging properties of the arrangement of supporting body 3 and membrane 5 are distinctly improved, which permits better and simpler optical detection of cells on the membrane.

This is facilitated by providing good transparency of the membrane-supporting plastic in the UV-A range (e.g., 337 nm).

Prior to the detection, the fluid-bearing channels between the supporting body 3 and the membrane 5 are filled with a liquid optical medium 11 with at least approximately the same refractive index as that of the membrane support (n=1.533) in such a manner that the biological sample on the membrane surface is still in contact with the optical medium. The preparation of an appropriate optical medium with a predetermined refractive index is known to the person skilled in the art. The refractive index of the optical medium (e.g., a sugar solution) can be determined with a refractometer and the solution can be adjusted appropriately by dilution. The vapor pressures of the components of the optical medium are preferably negligible.

Preferably in step D of FIG. 1 the optical analysis of the cells takes place from the reverse side, through the approximately 1 mm thick plastic support. This can be done, for example, with an inverse microscope. The arrow here indicates the direction from which the cell 9 is detected.

Then in an optional step E of FIG. 1 a detected target cell can be isolated by laser dissection.

The arrow in this case indicates the direction from which the cell 9 (and optionally a subarea of the membrane on which the cell is lying) is loosened from the membrane using a laser beam and captured by a sample vessel 13. The isolated cell can be subjected to additional tests.

The method according to an embodiment of the invention is particularly suitable for this combination with laser dissection, since the use of the optical medium makes particularly accurate work possible.

Alternatively, the cell can also remain on the membrane and be subjected to additional tests there, e.g., in an EPISPOT or EPISPOT (Enzyme Linked Immuno Spot Technique) process. In these processes, substances secreted by the cell are detected immunochemically on the membrane.

The invention claimed is:

1. A process for detecting cells to be detected in a liquid sample, comprising:
   i) filtrating the liquid sample through a porous membrane arrayed in a flat configuration on a transparent supporting body, wherein the porous membrane is suitable for retaining the cells to be detected, such that the cells to be detected are retained on at least part of a surface of the membrane and such that at least part of the liquid sample passes through the membrane, wherein the supporting body is a slide for microscopy, made of glass or plastic;
   ii) applying a liquid optical medium to the membrane on the transparent supporting body, wherein, the liquid optical medium has essentially the same refractive index as the transparent supporting body; and
   iii) optically measuring at least a subarea of the membrane on the transparent supporting body in order to detect the cells to be detected,
wherein the porous membrane remains in a flat configuration on the transparent support during the entire course of steps i)-iii).

2. The process of claim 1, wherein the cells to be detected are labeled before or after filtration with a first element for labeling the cells to he detected, which contains a first marker.

3. The process of claim 1, wherein
   the supporting body is at least one of textured, porous, and made of plastic.

4. The process of claim 1, wherein the support and the supporting body are made integrally from a single body and the membrane completely covers the supporting body.

5. The process of claim 1, wherein the supporting body includes channels formed on a side facing the filter membrane, said channels being configured in fluid contact with the membrane.

6. The process of claim, 1, wherein the membrane and the supporting body include a plurality of mutual contact points lying in a plane-parallel, flat plane of the contact surface, and wherein especially the membrane includes a maximum distance from the planar contact surface of less than 100 μm.

7. The process of claim 1, wherein the membrane is a Track Etched filter membrane that is composed of a polycarbonate film or and includes pores with a diameter of 2 μm-100 μm.

8. The process of claim 1, wherein at least one cell to be detected is isolated on the surface of the membrane after the filtrating the liquid sample through the porous membrane.

9. The process of claim 8, wherein the cell to be detected is isolated by laser microdissection.

10. The process of claim 1, wherein the cell to be detected is a tumor cell.

11. The process of claim 3, wherein the support is a slide for microscopy, made of COC.

12. The process of claim 3, wherein the supporting body is made of a same plastic as the support.

13. The process of claim 4, wherein the membrane lies flat on the supporting body.

14. The process of claim 2, wherein at least one of
the support is a slide for microscopy, made of glass or plastic; and
the supporting body is at least one of textured, porous, and made of plastic.

15. The process of claim 2, wherein the support and the supporting body are made integrally from a single body and the membrane completely covers the supporting body.

16. The process of claim 11, wherein the supporting body is made of a same plastic as the support.

17. The process of claim 12, wherein the membrane lies flat on the supporting body.

18. The process of claim 2, wherein the element for labeling comprises at least one marker that can stain cells specifically or nonspecifically.

19. The process of claim 18, wherein the nonspecific marker includes at least one of a dye that stain proteins, nucleic acids, or other cell constituents.

20. The process of claim 18, wherein the specific marker includes at least ore of an antibody, oligonucleotide probe, peptide or other molecule that binds specifically to proteins, nucleic acid sequences or other cell-specific structures.

* * * * *